United States Patent
Nakano

(10) Patent No.: US 9,146,217 B2
(45) Date of Patent: Sep. 29, 2015

(54) RACK WITH MOVABLE SHIELDING COMPONENT, AND AUTO-SAMPLER HAVING THE RACK

(75) Inventor: Tomohito Nakano, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/364,076

(22) Filed: Feb. 1, 2012

(65) Prior Publication Data

US 2012/0222502 A1 Sep. 6, 2012

(30) Foreign Application Priority Data

Mar. 4, 2011 (JP) .................................. 2011-047528

(51) Int. Cl.
*G01N 30/24* (2006.01)
*G01N 30/04* (2006.01)

(52) U.S. Cl.
CPC ................ *G01N 30/24* (2013.01); *G01N 30/04* (2013.01)

(58) Field of Classification Search
CPC ............................... G01N 30/04; G01N 30/24
USPC ........... 73/864.91; 422/65, 67, 68.1, 551, 552
See application file for complete search history.

(56) References Cited

U.S. PATENT DOCUMENTS

| 6,321,654 | B1* | 11/2001 | Robinson ...................... 102/251 |
| 7,109,481 | B1* | 9/2006 | Zanon et al. ................... 250/288 |
| 2008/0206098 | A1* | 8/2008 | Tsutsumida et al. ............ 422/67 |

FOREIGN PATENT DOCUMENTS

| JP | 06-034614 | 2/1994 |
| JP | 2010-014441 A | 1/2010 |

OTHER PUBLICATIONS

Chinese Office Action mailed on Aug. 28, 2013 for corresponding Chinese Patent App. No. 201210050230.X.

* cited by examiner

*Primary Examiner* — Hezron E Williams
*Assistant Examiner* — David Z Huang
(74) *Attorney, Agent, or Firm* — Morgan, Lewis & Bockius LLP

(57) ABSTRACT

A rack is provided wherein the type of micro-plate that is placed on the rack can be determined even when using one type of rack. The rack includes a bottom piece on which micro-plate is placed; at least one shielding component for recognizing the type of micro-plate; and a recognition unit having an enclosure disposed with a shielding component. When the rack is housed in a housing unit of an analyzer main unit, the shielding component is movable with respect to the enclosure so that the shielding component is positioned either in a detection position where detectable by a sensor or in a non-detection position where undetectable by the sensor.

6 Claims, 4 Drawing Sheets

PRIOR ART

RACK WITH MOVABLE SHIELDING COMPONENT, AND AUTO-SAMPLER HAVING THE RACK

TECHNICAL FIELD

The present invention relates to a rack on which micro-plates are placed and an auto-sampler having the rack. The rack can be used, for example, in auto-samplers that are used in liquid chromatographic analyzers.

BACKGROUND

Liquid chromatographic analyzers are used for analyzing liquid specimens. A liquid chromatographic analyzer uses a needle to collect liquid specimens, which are injected into an analysis flowpath. When doing this, the liquid specimen is contained in a test tube (container) that is made of transparent glass or plastic.

Liquid chromatographic analyzers are sometimes used to analyze many liquid specimens. This has led to liquid chromatographic analyzers that are equipped with auto-samplers (e.g., see Patent Literature 1). FIG. 5 shows a perspective view of a portion of a liquid chromatographic analyzer. FIG. 6 shows a perspective view of a portion of an auto-sampler. FIG. 7 shows a perspective view of a rack on which two micro-plates are placed.

The auto-sampler 101 includes: a control unit 160 and housing unit 170, which houses rack 120, both of which are disposed in the liquid chromatographic analyzer main unit 150; a plurality of types (e.g., 7 types) of micro-plates 10 for holding a plurality of test tubes; and a plurality of types (e.g., 7 types) of racks 120 on which micro-plates 10 are placed.

A first micro-plate 10 is a case made of plastic. The first micro-plate 10 has a substantially rectangular parallelepiped shape with, for example, a width (X) of 85 mm, length (Y) of 125 mm and height (Z) of 25 mm. A first hole 11 through a $45^{th}$ hole 11 are formed on the upper surface with five holes arranged in the X-direction (row direction) and nine holes arranged in the Y-direction (column direction). Each hole 11 is cylindrically-shaped which allows the lower half of a test tube to be inserted into a hole 11. The result is that 45 test tubes are held in the first micro-plate 10 arranged as described in the X-direction and the Y-direction.

Furthermore, a second micro-plate (not illustrated) is a case made of plastic. The second micro-plate has a substantially rectangular parallelepiped shape with, for example, a width (X) of 85 mm, length (Y) of 125 mm and height (Z) of 25 mm. A first hole through a $32^{nd}$ hole are formed on the upper surface with four holes arranged in the X-direction (row direction) and eight holes arranged in the Y-direction (column direction). Each hole is cylindrically-shaped which allows the lower half of a test tube to be inserted into a hole. The result is that 32 test tubes are held in the second micro-plate arranged as described in the X-direction and the Y-direction. In other words, different types of micro-plates are available, featuring different number of holes and different hole locations. The description of the third through the seventh micro-plate is omitted here.

The first rack 120 includes: a bottom piece 121 having, for example, a width (X) of 94 mm, length (Y) of 260 mm and height (Z) of 20 mm; a recognition unit 122 that is disposed at the front end (positive Y-direction end) of the bottom piece 121; and a grip part 123 that is formed at the rear end (negative Y-direction end) of the bottom piece 121. Two of the first micro-plates 10 can be placed in the Y-direction (column direction) on the upper surface of the bottom piece 121.

The first rack 120 is provided with a recognition unit 122 which allows the control unit 160 of the liquid chromatographic analyzer main unit 150 to automatically recognize the type of micro-plate 10 that is housed in the housing unit 170. The recognition unit 122 includes: an enclosure 124 that is made of resin and having a rectangular parallelepiped shape; and a first light-shielding plate 125 that is made of resin and protruding 4 mm out in the Y-direction from the enclosure 124.

The second rack (not illustrated) includes: a bottom piece having, for example, a width (X) of 94 mm, length (Y) of 260 mm and height (Z) of 20 mm; a recognition unit that is disposed at the front end (positive Y-direction end) of the bottom piece; and a grip part that is formed at the rear end (negative Y-direction end) of the bottom piece. Two of the second micro-plates can be placed in the Y-direction (column direction) on the upper surface of the bottom piece. A recognition unit includes: an enclosure that is made of resin and having a rectangular parallelepiped shape; and a first light-shielding plate and a second light-shielding plate both made of resin and protruding 4 mm out in the Y-direction and being aligned in the X-direction. In other words, the first rack 120 and the second rack have different number of light-shielding plates 125, and each micro-plate 10 has its own dedicated rack.

The housing unit 170 is provided with a plurality (e.g., three) of photosensors 71 at positions corresponding to the recognition unit 122 of the rack 120. Beach photosensor 71 includes: an emission unit 71a that emits light in the Z-direction; and a detection unit 71b which detects light from the emission unit 71a with a predetermined distance (e.g., 20 mm) of separation between them. Furthermore, a first photosensor 71, a second photosensor 71 and a third photosensor 71 are formed to be aligned with each other in the X-direction. In this way, if three photosensors 71 are provided, there are eight possible combinations in which photosensors 71 may be shielded or not shielded from light. Since it is desirable for the housing unit 170 to be able to automatically recognize the absence of rack 120, it is possible for the housing unit 170 to discriminate among 7 types of micro-plates 10, excluding the situation where none of the photosensors 71 is shielded from light.

The control unit 160 determines the type of micro-plate 10 that is housed in the housing unit 170 based on the status of the recognition information (light-shielding information) that is detected by the three photosensors 71.

For example, if the first rack 120 is housed in the housing unit 170, since the first rack 120 has the first light-shielding plate 125, the first photosensor 71 is shielded from light while the second photosensor 71 and the third photosensor 71 are not shielded from light. From this combination, it is determined that a first micro-plate 10 is housed in the housing unit 170. If a second rack is housed in the housing unit 170, since the second rack has both the first light-shielding plate and the second light-shielding plate, the first photosensor 71 and the second photosensor 71 are shielded from light while the third photosensor 71 is not shielded from light. From this combination, it is determined that a second micro-plate is housed in the housing unit 170.

PATENT LITERATURE

Patent Literature 1: Unexamined Patent Application Publication H06-034614.

SUMMARY OF THE INVENTION

However, with the afore-described rack 120, as many number of racks 120 is required as the number of different types of micro-plates 10. Even though it is possible to use one replaceable rack and to swap and replace different recognition units from among a plurality of types of available recognition units, even then, as many recognition units as the number of types of micro-plates 10 would be necessary.

Hence, it is the object of the present invention to provide a rack wherein one type of rack can accept and recognize a plurality of different types of micro-plates.

To solve the afore-described problems, the rack according to the present invention to be housed in a housing unit of an analyzer main unit comprises:

a bottom piece on which micro-plates are placed;

at least one shielding component for recognizing the type of micro-plate; and a recognition unit having an enclosure on which the shielding component is installed;

wherein:

when the rack is housed in the housing unit of the analyzer main unit, the shielding component is movable with respect to the enclosure so that the shielding component is positioned at either a detection position detectable by a sensor that is installed on the housing unit of the analyzer main unit or a non-detection position undetectable by the sensor.

With a rack according to the present invention, when, for example, a person performing the analysis places a first micro-plate on the rack, a first shielding component is moved to the detection position. The rack is then placed in the housing unit of the analyzer main unit. This causes the first sensor, but not the second sensor, to detect the shielding component, resulting in the analyzer main unit to recognize what is housed as a first micro-plate. If the person performing the analysis places a second micro-plate on the rack, the first shielding component and the second shielding component are moved to the detection positions. The rack is then placed in the housing unit of the analyzer main unit. This causes the first sensor and the second sensor to detect the shielding components and the analyzer main unit to recognize that the second micro-plate is housed. Furthermore, if the person performing the analysis places a third micro-plate on the rack, the second shielding component is moved to the detection position. The rack is then placed in the housing unit of the analyzer main unit. This causes the second sensor, but not the first sensor, to detect the shielding component, resulting in the analyzer main unit to recognize the presence of a third micro-plate.

As afore-described, with a rack according to the present invention, any one of a plurality of different types of micro-plates that is placed on a rack can be recognized while using only one type of rack.

With the rack according to the present invention, the sensors may comprise an emission unit for emitting light and a detection unit for detecting, from a predetermined distance away, the light from the emission unit. The shielding component may be positioned at either a detection position or a non-detection position situated between the emission unit and the detection unit.

Here, the term "predetermined distance" refers to any distance that allows the insertion of the shielding component.

Furthermore, with the rack according to the present invention, the analyzer main unit is provided with a plurality of sensors, and the enclosure for the recognition unit is provided with a plurality of shielding components. Each of the shielding components are made to be independently movable with respect to the enclosure.

Furthermore, with the rack according to the present invention, formed on an upper surface of the enclosure of the recognition unit are movement grooves comprising a front-end portion and a rear-end portion having an increased width in plan view and a coupling part having a narrow width and coupling the front-end portion and the rear-end portion; and formed on the shielding component is a vertically extending protruding part whose top portion has a width narrower than the width of its bottom portion; the top portion of the protruding part passing through the movement groove in the horizontal direction while penetrating vertically through the coupling part of the movement groove; the bottom portion of the protruding part passing through the movement groove in the horizontal direction while penetrating vertically through the coupling part of the movement groove; and the shielding component being movable with respect to the enclosure when the protruding part is pressed downwardly.

The auto-sampler according to the present invention includes: a rack as afore-described; a plurality of types of micro-plates for holding a plurality of containers; and control unit and a housing unit for housing the racks, both of which are disposed on the analyzer main unit; wherein sensors are disposed on the housing unit, and the control unit determines the type of micro-plate based on recognition information from the sensors.

DETAILED DESCRIPTION OF THE INVENTION

Embodiments of the present invention are described next with reference to figures. It should be noted that the present invention is not limited to the embodiments described below, and needless to say, various modifications are possible without deviating from the gist of the present invention.

Figure 1:
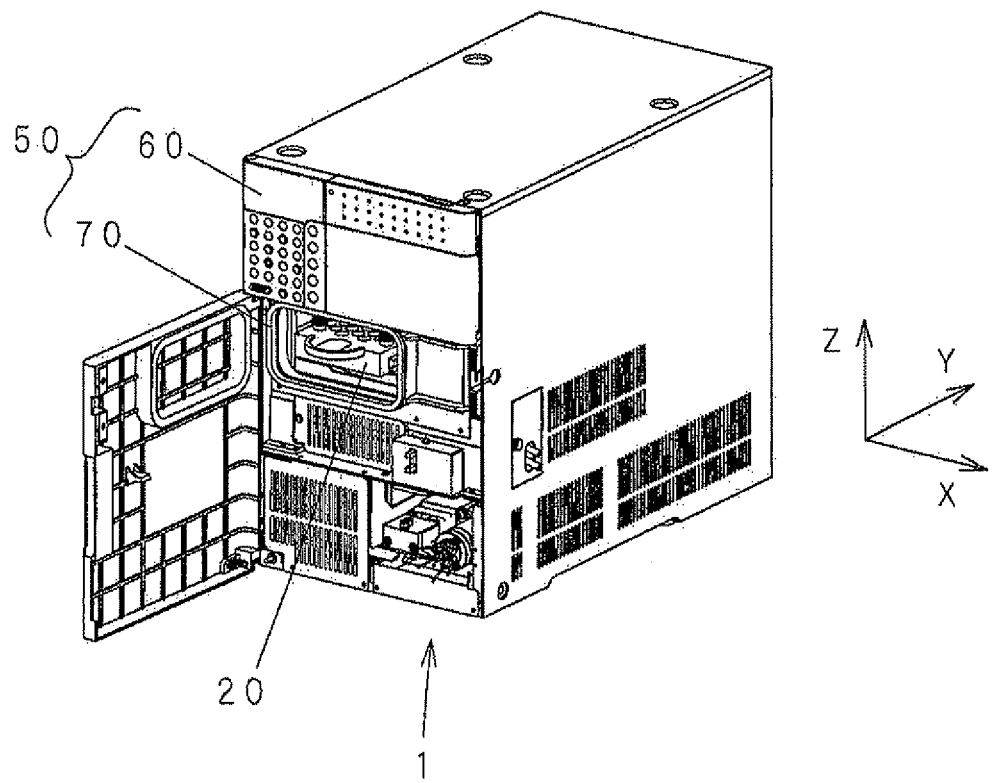
FIG. 1 shows a perspective view of a part of a liquid chromatographic analyzer that relates to the present invention.
Figure 2:
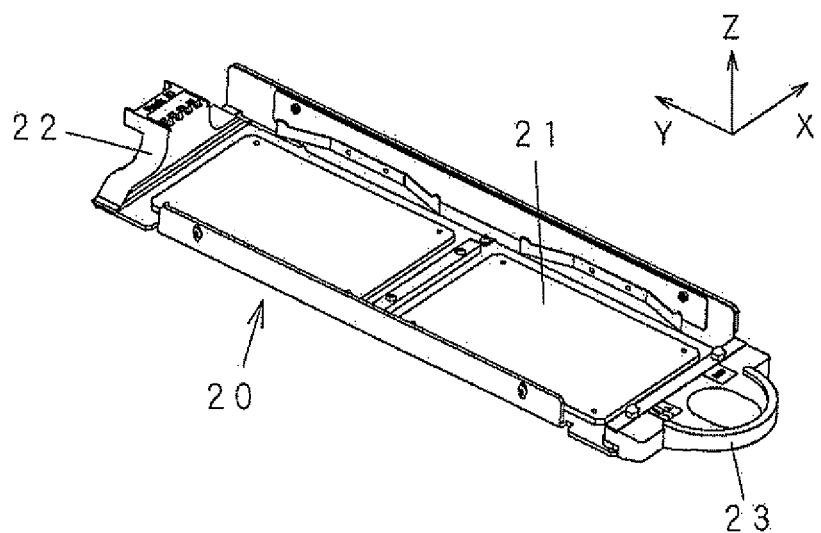
FIG. 2 shows a perspective view of one example of rack according to the present invention.

FIG. 1 shows a perspective view of a part of a liquid chromatographic analyzer according to the present invention. FIG. 2 shows a perspective view of a part of a rack according to the present invention. The same numerical references are used for the same components that appear in the description above of the auto-sampler 101.

The auto-sampler 1 includes: a control unit 60 and a housing unit 70 in which racks 20 are housed, both units being provided in the liquid chromatographic analyzer main unit 50; a plurality of types (e.g., 7 types) of micro-plates 10 for holding a plurality of test tubes; and one type of rack 20 on which a plurality of types (e.g., 7 types) of micro-plates 10 is placed.

The rack 20 includes: a bottom piece 21 having, for example, width (X) of 94 mm, length (Y) of 260 mm and height (Z) of 20 mm; a recognition unit 22 that is disposed at the front end (positive Y-direction end) of the bottom piece 21; and a grip part 23 that is formed at the rear end (negative Y-direction end) of the bottom piece 21. Two micro-plates 10 of different types are placed next to each other in the Y-direction (column direction) on the upper surface of the bottom piece 21.

Figure 3:
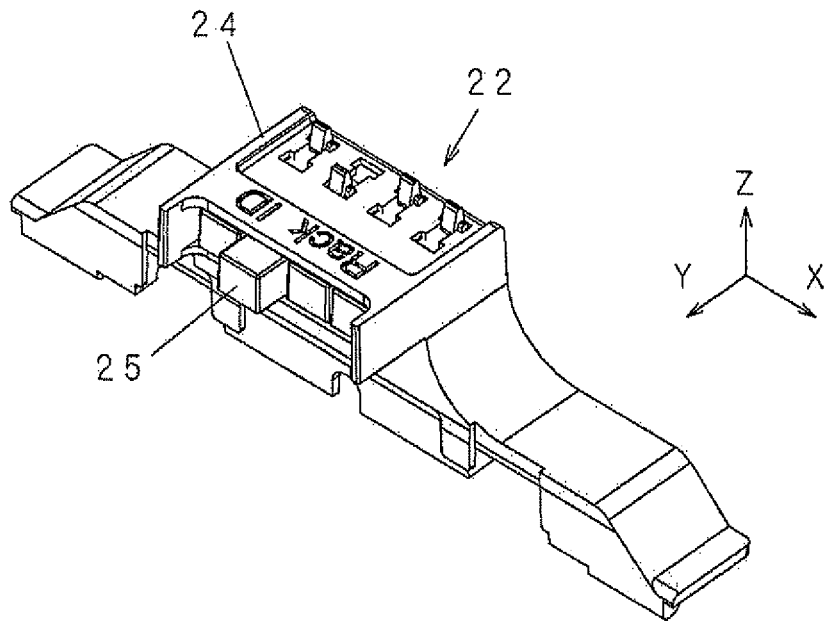
FIG. 3 shows a perspective view of the recognition unit that is shown in FIG. 2.
Figure 4:
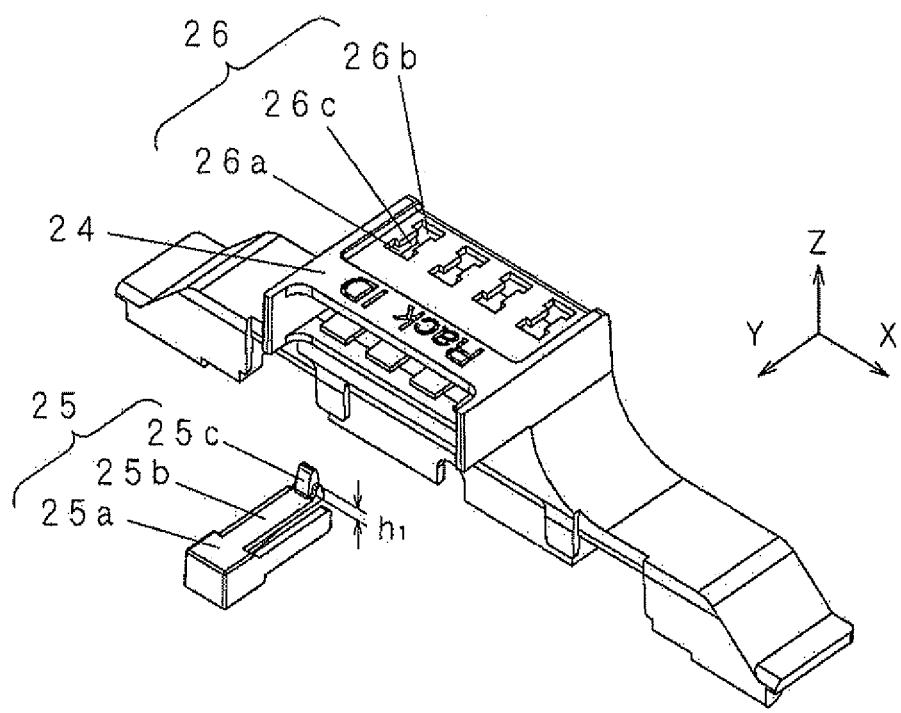
FIG. 4 shows an exploded perspective view of the recognition unit shown in FIG. 3.
Figure 5:
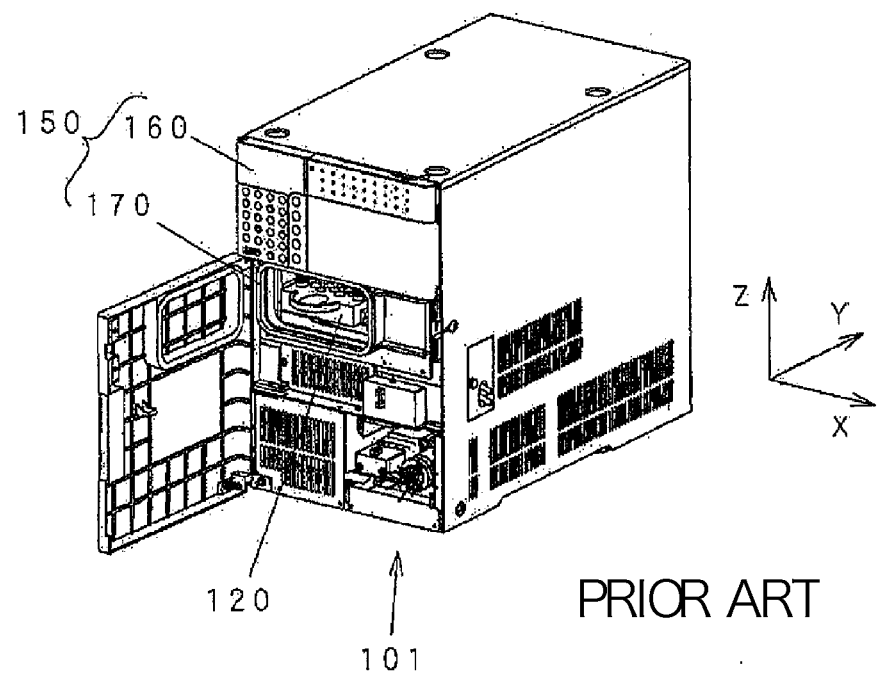
FIG. 5 shows a perspective view of a part of the liquid chromatographic analyzer.

FIG. 3 shows a perspective view of the recognition unit 22 that is shown in FIG. 2. FIG. 4 shows an exploded perspective view of the recognition unit 22 shown in FIG. 3. The recognition unit 22 includes: a resin-made enclosure 24 in the shape of a quadrangular cylinder lying on its side with the central axis about the Y-direction; and four resin-made light-shielding components 25 that are installed on the interior of the enclosure 24.

Formed on the upper surface of enclosure 24 are four movement grooves 26 that penetrate through the upper surface of enclosure 24. In plan view, each movement groove 26 is shaped like the letter "I" with a quadrangular front-end portion 26a with a broad width (X), a quadrangular rear-end portion 26b with a broad width (X) and a rectangular coupling part 26c having a narrow width (X) and joining the front-end portion 26a and the rear-end portion 26b in the Y-direction. The first movement groove 26, second movement groove 26, third movement groove 26 and fourth movement groove 26 are successively lined up in the X-direction. Furthermore, formed on the top portion of the lower surface of the enclosure 24 at positions corresponding to the movement grooves 26 are four rails (not illustrated) extending in the Y-direction.

The light-shielding component 25 includes: a black rectangular parallelepiped-shaped light-shielding part 25a; a leaf spring part 25b extending from the top of the light-shielding part 25a in the negative Y-direction; and a protruding part 25c that extends from the tip of the leaf spring part 25b in the Z-direction (upwardly). With the protruding part 25c, the width (X) of the top portion (located higher than height $h_1$) is narrower than the width (X) of the bottom portion (located lower than height $h_1$). This arrangement means that the top portion of the protruding part 25c penetrates through the coupling part 26c of the movement groove 26 in the Z-direction while passing through the coupling part 26c of the movement groove 26 in the Y-direction, and the bottom portion of the protruding part 25c penetrates through the coupling part 26c of the movement groove 26 in the Z-direction while passing through the coupling part 26c of the movement groove 26 in the Y-direction. This means that when the light-shielding component 25 is attached to the movement groove 26 and the person performing the analysis presses in the protruding part 25c by distance $h_1$, the light-shielding component 25 moves in the Y-direction relative to the enclosure 24. On the other hand, if the protruding part 25c is not pushed in and either the front-end portion 26a or the rear-end portion 26b is penetrated through, the light-shielding component 25 becomes fixed to the enclosure 24. At this time, if the protruding part 25c is located at the position of the front-end portion 26a, the light-shielding component 25 protrudes from the enclosure 24 by 4 mm in the Y-direction in a protruded state (detection position). On the other hand, if the protruding part 25c is located at the position of the rear-end portion 26b, the light-shielding component 25 remains contained (no-detection position) within the enclosure 24.

Figure 6:
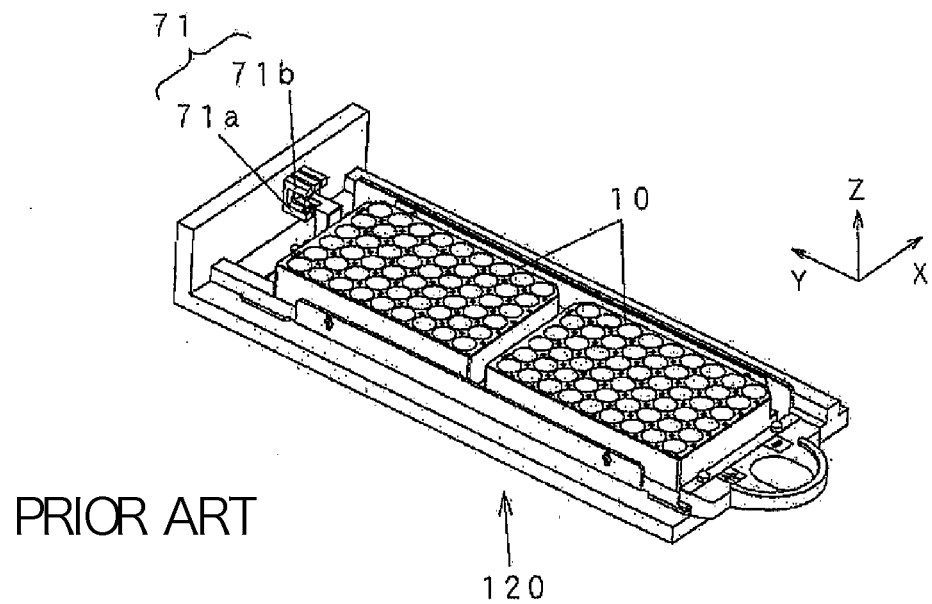
FIG. 6 shows a perspective view of a part of an auto-sampler.
Figure 7:
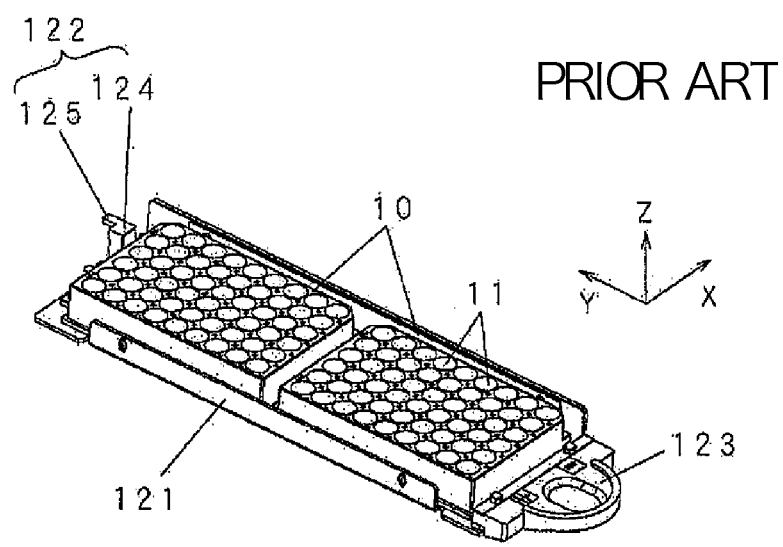
FIG. 7 shows a perspective view of a rack with two micro-plates placed thereon.

After that, the first light-shielding component 25 is installed in the first movement groove 26, the second light-shielding component 25 is installed in the second movement groove 26, the third light-shielding component 25 is installed in the third movement groove 26, and the fourth light-shielding component 25 is installed in the fourth movement groove 26. This results in rack 20 to be housed in the housing unit 70 of the liquid chromatographic analyzer main unit 50. If the first light-shielding component 25 is in the protruded state, first light-shielding component 25 becomes interposed between the emission unit 71a of the first photosensor 71 and the detection unit 71b (see FIG. 6). On the other hand, if the first light-shielding component 25 remains contained within the enclosure, the first light-shielding component 25 is not interposed between the emission unit 71 of the first photosensor 71 and the detection unit 71b. Also, if the second light-shielding component 25 is in the protruded state, the second light-shielding component 25 becomes interposed between the emission unit 71a of the second photosensor 71 and the detection unit 71b. On the other hand, if the second light-shielding component 25 is contained within the enclosure, the second light-shielding component 25 is not interposed between the emission unit 71a of the second photosensor 71 and the detection unit 71b. The third light-shielding component 25 and the fourth light-shielding component 25 are positioned similarly as the first light-shielding component 25 with respect to the third photosensor 71 and the fourth photosensor 71, respectively.

On the housing unit 70, a plurality (e.g., 4) of photosensors 71 is disposed at positions corresponding to the recognition unit 22 of the rack 20. Each photosensor 71 includes: an emission unit 71a that emits light in the Z-direction; and a detection unit 71b that detects light from the emission unit 71a with a predetermined distance (e.g., 20 mm) of separation. First photosensor 71, second photosensor 71, third photosensor 71 and fourth photosensor 71 are formed to be successively lined up in the X-direction. By disposing the four photosensors 71 as afore-described, there are 16 different ways in which light from photosensors 71 can be shielded or not shielded. Incidentally, since it is desirable for the absence of a rack 20 in the housing unit 70 to be automatically recognized, a total of 15 types of micro-plates 10 can be recognized, not including the situation where none of the photosensors 71 is shielded from the light.

The control unit 60 uses the recognition information (light-shielding information) detected by the four photosensors 71 to determine the type of micro-plate 10 that is housed in the housing unit 70.

For example, when the person performing the analysis places a first micro-plate 10 on rack 20, the first light-shielding component 25 is moved to create a protruded state (detection position), and the second through the fourth light-shielding components 25 are moved to the contained state (no-detection position). Rack 20 is then placed in the housing unit 70 of the liquid chromatographic analyzer main unit 50. This causes the first photosensor 71 to detect the presence of the light-shielding component, and the second through the fourth photosensors 71 to not detect the presence of a light-shielding component 25. As a result, the control unit 60 recognizes that a first micro-plate 10 is housed within the enclosure.

Also, when the person performing the analysis places a second micro-plate on the rack 20, the first light-shielding component 25 and the second light-shielding component 25 are moved to the protruded state (detection position), and the third through the fourth light-shielding components 25 are moved to the contained state (non-detection position). The rack 20 is then placed in the housing unit 70 of the liquid chromatographic analyzer main unit 50. This causes the first photosensor 71 and the second photosensor 71 to detect the presence of the light-shielding components 25, and the third through the fourth photosensors 71 to not detect the light-shielding component 25. The result is for the control unit 60 to recognize the micro-plate as a second micro-plate.

In this way, the person performing the analysis places a micro-plate 10 of a certain type on the rack 20 and moves the light-shielding components 25 that correspond to that certain type of micro-plate 11 to the protruded state (detection position). The control unit 60 then determines the type of micro-plate 10 that is housed in the housing unit 70. Information regarding the positioning of the light-shielding components 25 and the corresponding type of micro-plate 10 is stored in advance in the control unit 60.

As afore-described, one type of rack 20 can accommodate a variety of types of micro-plates 10 and still recognize particular types of micro-plate 10.

Other Embodiments

The afore-described auto-sampler 1 was equipped with photosensors 71 but other devices such as microswitches and magnetic sensors may be used instead.

The present invention can be used with racks and the like that are used with auto-samplers that are used with liquid chromatographic analyzers.

DESCRIPTION OF THE NUMERICAL REFERENCES

10: Micro-plate
20: Rack
21: Bottom piece
22: Recognition unit
24: Enclosure
25: Light-shielding component (shielding component)
50: Analyzer main unit
70: Housing unit
71: Sensor (photosensor)

What is claimed is:

1. A rack for housing in a housing unit of an analyzer main unit, said rack comprising:
   a bottom piece on which one of micro-plates is placed;
   at least one shielding component for recognizing the types of said micro-plates; and
   a recognition unit having an enclosure within which said shielding component is installed, the recognition unit being disposed at the front end of the bottom piece,
   wherein said shielding component is individually configured to be moved relative to the enclosure and the rack so that when the rack is housed in the housing unit of said analyzer main unit, said shielding component is positioned at either a detection position detectable by a sensor that is installed on the housing unit of said analyzer main unit or a non-detection position undetectable by said sensor.

2. The rack according to claim 1, said sensor comprising:
   an emission unit for emitting light; and
   a detection unit positioned a predetermined distance away for detecting light from said emission unit,
   wherein said shielding component is positioned at either the detection position located between said emission unit and said detection unit or the non-detection position located between said emission unit and said detection unit.

3. The rack according to claim 1 wherein a plurality of sensors is disposed on the housing unit of said analyzer main unit; and
   a plurality of shielding components is installed on the enclosure of said recognition unit, each shielding component being individually movable with respect to said enclosure.

4. An auto-sampler comprising:
   a rack described in claim 1;
   a plurality of types of micro-plates for holding a plurality of containers; and
   a housing unit for housing said racks and a control unit, both of which are disposed on the analyzer main unit,
   wherein said sensors are disposed on said housing unit; and
   said control unit determines the type of said micro-plate based on recognition information from said sensors.

5. A rack for housing in a housing unit of an analyzer main unit, said rack comprising:
   a bottom piece on which one of micro-plates is placed;
   at least one shielding component for recognizing the type of said micro-plate; and
   a recognition unit having an enclosure within which said shielding component is installed,
   wherein when the rack is housed in the housing unit of said analyzer main unit, said shielding component is movable with respect to said enclosure so that said shielding component is positioned at either a detection position detectable by a sensor that is installed on the housing unit of said analyzer main unit or a non-detection position undetectable by said sensor, and
   wherein formed on an upper surface of the enclosure of said recognition unit are movement grooves comprising a front-end portion and a rear-end portion having an increased width in plan view and a coupling part having a narrow width and coupling the front-end portion and the rear-end portion; and
   formed on said shielding component is a vertically extending protruding part whose top portion has a width narrower than the width of its bottom portion;
   the top portion of said protruding part passing through said movement groove in the horizontal direction while penetrating vertically upward through the coupling part of said movement groove;
   the bottom portion of said protruding part passing through said movement groove in the horizontal direction while penetrating vertically downward through the coupling part of said movement groove; and
   said shielding component being movable with respect to said enclosure when said protruding part is pressed downwardly.

6. A rack for housing in a housing unit of an analyzer main unit, said rack comprising:
   a bottom piece on which one of micro-plates is placed;
   a plurality of shielding components for recognizing the types of said micro-plates;
   a plurality of sensors installed on the housing unit of said analyzer main unit; and
   a recognition unit having an enclosure within which each shielding component is installed,
   wherein each shielding component is individually moved relative to the enclosure and the rack so that when the rack is housed in the housing unit of said analyzer main unit, each shielding component is positioned at either a detection position detectable by a corresponding sensor from the plurality of sensors or a non-detection position undetectable by said corresponding sensor.

* * * * *